United States Patent [19]

Hinz et al.

[11] Patent Number: 5,785,962
[45] Date of Patent: Jul. 28, 1998

[54] HAIR SHAMPOO

[75] Inventors: Sabine Hinz, Pfungstadt; Dieter Heinz, Gustavsburg, both of Germany

[73] Assignee: Goldwell GmbH, Germany

[21] Appl. No.: 801,097

[22] Filed: Feb. 14, 1997

Related U.S. Application Data

[63] Continuation of Ser. No. 599,492, Jan. 24, 1996, abandoned.

[30] Foreign Application Priority Data

Feb. 15, 1995 [DE] Germany .................. 195 04 914.4

[51] Int. Cl.$^6$ .................................................. A61K 7/075
[52] U.S. Cl. ............................. 424/70.22; 424/70.19
[58] Field of Search ............................. 424/70.1, 70.19, 424/70.21, 70.22, 70.31; 510/119, 124, 125, 127

[56] References Cited

U.S. PATENT DOCUMENTS

| | | | |
|---|---|---|---|
| 4,670,185 | 6/1987 | Fujiwara et al. | 252/311 |
| 5,053,222 | 10/1991 | Takasu et al. | 514/852 |
| 5,376,643 | 12/1994 | Sugiyama et al. | 424/70.6 |
| 5,439,682 | 8/1995 | Wivell et al. | 424/70.21 |
| 5,466,396 | 11/1995 | Madison et al. | 252/557 |
| 5,716,625 | 2/1998 | Hahn et al. | 424/401 |

*Primary Examiner*—Robert H. Harrison
*Attorney, Agent, or Firm*—Londa and Traub LLP

[57] ABSTRACT

The invention comprises a shampoo composition providing the hair with improved properties such as combability, volume and lustre, containing at least one anionic, nonionic and (or) zwitterionic (amphoteric) surfactant and a mixture of a) at least 0.1% by wt. lactic acid;
b) at least 0.05% by wt. citric acid; and
c) at least 0.05% by wt. pyrrolidone carboxylic acid, all percentages being calculated to the total composition.

15 Claims, No Drawings

HAIR SHAMPOO

This application is a continuation of application Ser. No. 08/599,492, filed Jan. 24, 1996, abandoned.

This invention comprises a liquid hair shampoo in an aqueous medium which has a conditioning effect on the hair, providing the hair with lustre and volume as well as improved combability in wet and dry state and, particularly when used on dry hair, imparting lustre, softness and pliability.

According to the invention, a shampoo comprising these improved properties contains at least one anionic, nonionic, and (or) zwitterionic surfactant and a mixture of at least 0.1% by wt. lactic acid, at least 0.05% by wt. citric acid, and at least 0.05% by wt. pyrrolidone carboxylic acid (i.e., 5-oxo-pyrrolidine-2-carboxylic acid, also known under the term "pyroglutamic acid"), all percentages being calculated to the total composition.

The addition of this mixture to conventional shampoos gives them the properties described above.

The effect of these hair shampoos according to the invention can even be improved by the addition of further organic acids selected from the group of glycolic acid, malic acid, glyoxylic acid, tartaric acid and (or) pyruvic acid, preferably in a proportion of at least 0.01%, particularly at least 0.05% by wt., calculated to the total composition.

The upper limit of these organic acids is not critical and is mainly determined by the desired pH-value of the shampoo according to the invention. The total proportion of the above referred organic acids shall not exceed a maximum of about 5% by wt., preferably about 2.5% by wt., calculated to the total composition.

The minimum proportion is about 0.20%, particularly 0.5% by wt. These organic acids may be added as such or also as an ingredient in plant and fruit juices or extracts.

The preferred pH-value of the shampoo is about 4 to 7, particularly between about 5 and 5.5.

Another preferred ingredient of the shampoos according to the invention is glycerol in a minimum quantity of about 0.5% by wt., preferably about 1% to about 10% by wt., of the composition.

Preferred surfactants within the scope of the invention are anionic surfactants in a proportion of at least 5% to about 40% by wt. of the composition, or the composition may contain from 5% to 50% by weight, calculated to the total composition, of at least on anionic surfactant.

Suitable anion-active surfactants are of the sulfate, sulfonate, carboxylate, and alkyl phosphate type, particularly of course those normally used in shampoos, e.g., the known $C_{10}$–$C_{18}$-alkyl sulfates and particularly the corresponding ether sulfates, e.g., $C_{12}$–$C_{14}$-alkyl ether sulfate, lauryl ether sulfate, having especially 1 to 4 ethylene oxide groups in their molecules, furtheron monoglyceride sulfates, fatty acid amide sulfates prepared by ethoxylation and subsequent sulfation of fatty acid alkanol amides and the alkali salts thereof, as well as salts of long-chain mono- and dialkyl phosphates which are mild and skin-compatible detergents.

Further suitable anionic surfactants within the scope of the invention are α-olefin sulfonates or their salts, particularly alkali salts of sulfosuccinic acid semi-esters, for instance disodium salt of monooctyl sulfosuccinate and alkali salts of long-chain monoalkyl ethoxysulfosuccinates.

Suitable surfactants of the carboxylate type are alkyl polyether carboxylic acids and their salts of the formula R—(C$_2$H$_4$O)$_n$—O—CH$_2$ COOX, wherein R denotes a $C_8$–$C_{20}$-alkyl group, preferably a $C_{12}$–$C_{14}$-alkyl group, n is a number from 1 to 20, preferably from 2 to 17, and X is H or preferably a cation of the group of sodium, potassium, magnesium and ammonium, which may optionally be substituted by alkyl hydroxyalkyl, and alkyl amidopolyether carboxylic acids of the general formula $$R-\underset{\underset{O}{\|}}{C}-\underset{\underset{H}{|}}{N}-CH_2-CH_2-(C_2H_4O)_n-O-CH_2COOX.$$

These products have been known for some time and are available on the market, e.g. under the trade names "AKYPO" and "AKYPO-SOFT®".

It is particularly suitable to use mixtures of several anionic surfactants, e.g., a mixture of α-olefin sulfonate with a sulfosuccinate, preferably in a proportion of from 1:3 to 3:1.

Protein-fatty acid condensation products of essentially known structure may also be used in admixture with other anionic surfactants, particularly in a proportion between about 0.5% and 5%, preferably between 1% and 3% by wt. of the total composition of the liquid shampoo.

A survey of anion-active surfactants used in liquid body cleansing compositions is given in the monography of K.Schrader, "Grundlagen und Rezepturen der Kosmetika", 2nd Ed. (1989, Hüthig Buchverlag, Heidelberg), pp.683 to 691.

The preferred proportion range of anionic surfactants in the liquid shampoos according to the invention is between about 5% and about 35% by wt., particularly about 7.5% to about 25% by wt., most preferred about 10% to about 20% by wt., calculated to the total composition.

Within the scope of the invention, nonionic surfactants are used preferably in admixture with anion-active surfactants.

In this context, a preferred nonionic surfactant belongs to the class of alkyl polyglucosides of the general formula R—O—(R$^1$O)$_n$—Z$_x$, wherein R denotes an alkyl group having 8 to 18 carbon atoms, R$^1$ is an ethylene or propylene group, Z is a saccharide residue with 5 to 6 carbon atoms, n is a number from 0 to 10, and x stands for a number between 1 and 2.5.

These alkyl polyglucosides have recently become known especially as excellent skin-compatible and lather-promoting ingredients in general liquid and body cleansing compositions.

Further nonionic surfactant components, e.g., are long-chain fatty acid mono- and dialkanolamides, for instance coconut fatty acid monoethanolamide and myristic fatty acid monoethanolamide, which can be also employed as foam enhancers.

Other nonionic surfactants, e.g., are the various sorbitan esters such as polyethylene glycol sorbitan stearic acid ester, fatty acid polyglycol ester or also mixed condensates of ethylene oxide and propylene oxides as they are on the market, e.g., under the trade name "Pluronics".

Mixtures of anion-active surfactants with alkyl polyglucosides, the preferred nonionic surfactants within the scope of the invention, as well as their use in liquid body cleansing compositons are basically known, e.g., from European Patent No. 70,074. On principle, the alkyl polyglucosides described therein are also suitable within the scope of the present invention; this applies also to mixtures of sulfosuccinates and alkyl polyglucosides disclosed in European Patent No. 358,216.

Other surfactants, which may be used in admixture with anion-active surfactants, are amine oxides in a proportion of about 0.25% to about 5%, preferably about 0.5% to about 3.5% by wt., calculated to the total composition.

Since a long time, such amine oxides have been part of prior art, e.g., $C_{12}$–$C_{18}$-alkyl dimethyl amine oxide such as lauryl dimethyl amine oxide, $C_{12}$–$C_{18}$-alkyl amidopropyl or -ethyl amine oxide, $C_{12}$–$C_{18}$-alkyl di(hydroxyethyl) or (hydroxypropyl) amine oxide, or also amine oxides having ethylene oxide and (or) propylene oxide groups in their alkyl chains.

These amine oxides are on the market, e.g., under the trade names "Ammonyx®", "Aromox®" or "Genaminox®".

As further optional surfactants, the compositions according to the invention comprise amphoteric or zwitterionic surfactants, again preferably in mixture with anionic surfactants, in a proportion of about 0.1% to about 5%, preferably about 0.5% to about 3% by wt., calculated to the total composition. As such, the various known betaines such as fatty acid amido alkyl betaines and sulfobetaines, e.g. lauryl hydroxysulfobetaine, are mentioned; long-chain alkyl amino acids have also proved to be suitable.

In detail, betaines of the following structure may be used:

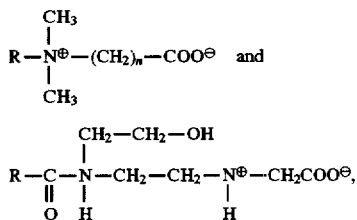

wherein R denotes a $C_8$–$C_{18}$-alkyl group and n is 1 to 3; sulfobetaines of the structure

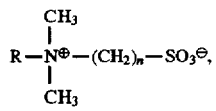

wherein R denotes a $C_8$–$C_{18}$-alkyl group and n is 1 to 3; and amidoalkyl betaines of the structure

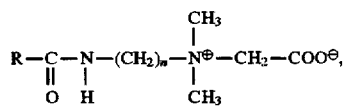

wherein R denotes a $C_8$–$C_{18}$-alkyl group and n is 1 to 3; long-chain alkyl amino carboxylic acids may also be used.

Naturally, the shampoos according to the invention may contain any other ingredients which are normally used in these compositions.

Complexing agents, dyestuffs, preservatives, pH-regulants, viscosity modifiers such as inorganic salts, unless these are generally included in the basic surfactant mixture, fragrances, pearl gloss agents, thickeners, humectants, plant and animal oils such as jojoba oil, etc. are mentioned as examples for this purpose.

A list of these additives is also found in Schrader, l.c., pp. 695 to 722.

Particularly suitable additives for shampoos are hair conditioning actives. Cationic polymers, preferably in a proportion between 0.1% to 2%, particularly 0.25% to 1.25% by wt. of the total composition, are specially used for this purpose.

European Patent No. 337,354 discloses the use of cationic polymers together with alkyl polyglucoside surfactants; the cationic polymers listed therein on pp.3 to 7 are also suitable as conditioning additives in the compositions of the invention.

Further conditioning additives are the well-known protein hydrolyzates, e.g. in a quantity from 0.25 to 5% by wt., preferably 0.5% to 2.5% by wt. of the total composition.

Additionally suitable, too, are water-soluble collagen or water-soluble collagen derivatives.

As it is already known, the various polysiloxanes may finally also be used as conditioning components in the liquid shampoo compositions according to the invention. Their preferred proportion is about between 0.5% and about 5%, particularly 1% to 3% by wt. of the total composition. Suitable are highly volatile as well as less volatile cyclic or linear polysiloxanes, i.e. silicone oils, e.g., known under their trivial names "Dimethicone" or "Phenyldimethicone" and "Cyclomethicone".

The silicone derivatives described in European Patent No. 398,177, which are used therein in combination with alkyl polyglucosides in liquid detergent compositions, are also suitable.

The shampoos according to the invention may also contain dyestuffs for direct or oxidative dyeing of hair, i.e. so-called tinting or coloring shampoos.

The following examples illustrate the invention in detail.

The preparation of the compositions according to the invention is effected by combining and mixing of the single components in water, whereby premixes of different ingredients may also be used.

EXAMPLE 1

| Shampoo for normal hair | |
|---|---|
| Sodium lauryl ether sulfate | 9.00 (% by wt.) |
| Disodium lauryl ether sulfosuccinate | 3.00 |
| Decyl glucoside (P.D.: ≈1.5) | 2.00 |
| PEG-55-propylene glycol oleate | 2.00 |
| PEG-160-sorbitan tristearate | 0.30 |
| PEG-3-distearate (opacifying agent) | 1.90 |
| Hydroxypropyl guar trimonium chloride | 0.30 |
| Panthenol | 0.30 |
| Lactic acid | 0.10 |
| Citric acid | 0.10 |
| Pyrrolidone carboxylic acid | 0.07 |
| Tartaric acid | 0.05 |
| Glycerol | 1.00 |
| Burr root oil | 0.10 |
| Perfume | 0.60 |
| Preservatives | 0.35 |
| Sodium chloride | 1.20 |
| Water | @ 100.00 |

Hair treated with this shampoo presented distinctly improved lustre, better wet and dry combability and more volume compared with hair treated with a shampoo of identical composition excluding, however, the mixture of lactic acid, citric acid, pyrrolidone carboxylic acid and tartaric acid.

EXAMPLE 2

| Shampoo for permanently waved hair | |
|---|---|
| Sodium lauryl ether sulfate | 5.00 (% by wt.) |
| Decyl glucoside (P.D.: ≈1.5) | 2.50 |
| PEG-55-propylene glycol oleate | 1.50 |

-continued

| Shampoo for permanently waved hair | |
|---|---|
| Coconut amidopropyl betaine | 1.50 |
| Lauryl hydroxysultaine | 0.80 |
| PEG-3-distearate (opacifier) | 1.90 |
| Quaternary cellulose derivative (Polymer JR 400) | 0.40 |
| Panthenol | 0.30 |
| Lactic acid | 0.10 |
| Citric acid | 0.10 |
| Pyrrolidone carboxylic acid | 0.07 |
| Tartaric acid | 0.05 |
| Glyoxylic acid | 0.03 |
| Malic acid | 0.03 |
| Pyruvic acid | 0.05 |
| Glycolic acid | 0.05 |
| Glycerol | 1.00 |
| Almond oil | 0.10 |
| Perfume | 0.60 |
| Wheat protein hydrolyzate | 0.30 |
| Preservatives | 0.35 |
| Sodium chloride | 0.50 |
| Water | @ 100.00 |

An improved effect was achieved compared with the shampoo of Example 1.

EXAMPLE 3

| Shampoo for colored hair | | |
|---|---|---|
| Sodium lauryl ether sulfate | 5.00 | (% by wt.) |
| Coconut amidopropyl betaine | 1.50 | |
| Decyl glucoside (P.D.: =1.5) | 2.00 | |
| PEG-55-propylene glycol oleate | 1.50 | |
| Lauryl hydroxysultaine | 0.80 | |
| PEG-3-distearate (opacifier) | 1.90 | |
| Quaternary cellulose derivative (Polyquaternium-10) | 0.40 | |
| Panthenol | 0.30 | |
| Lactic acid | 0.10 | |
| Citric acid | 0.10 | |
| Pyrrolidone carboxylic acid | 0.07 | |
| Tartaric acid | 0.05 | |
| Glyoxylic acid | 0.03 | |
| Malic acid | 0.03 | |
| Pyruvic acid | 0.05 | |
| Glycolic acid | 0.05 | |
| Glycerol | 1.00 | |
| Triglycerol | 0.20 | |
| Perfume | 0.60 | |
| Aloe oil | 0.10 | |
| Preservatives | 0.35 | |
| Wheat protein hydrolyzate | 0.30 | |
| Sodium chloride | 0.50 | |
| Water | @ 100.00 | |

The effect of this product was very similar to that of the composition according to Example 2.

EXAMPLE 4

| Shampoo for dry hair | | |
|---|---|---|
| Sodium lauryl ether sulfate | 6.00 | (% by wt.) |
| Disodium lauryl ether sulfosuccinate | 5.00 | |
| Decyl glucoside (P.D.: =1.5) | 5.00 | |
| Lauryl hydroxysultaine | 0.90 | |
| PEG-160-sorbitan tristearate | 1.00 | |
| PEG-3-distearate (opacifier) | 2.30 | |
| Quaternary cellulose derivative (Polyquaternium-10) | 0.40 | |
| Wheat germ oil | 0.10 | |
| Panthenol | 0.30 | |

-continued

| Shampoo for dry hair | |
|---|---|
| Lactic acid | 0.10 |
| Citric acid | 0.50 |
| Pyrrolidone carboxylic acid | 0.10 |
| Tartaric acid | 0.10 |
| Malic acid | 0.10 |
| Pyruvic acid | 0.10 |
| Glycerol | 1.50 |
| Triglycerol | 0.50 |
| Perfume | 0.60 |
| Wheat protein hydrolyzate | 1.00 |
| Preservatives | 0.35 |
| Sodium chloride | 0.75 |
| Water | @ 100.00 |

Using this shampoo provided the hair with better lustre, volume and excellent wet and dry combability, compared with a conventional shampoo.

EXAMPLE 5

| Antidandruff shampoo | | |
|---|---|---|
| Sodium lauryl ether sulfate | 7.50 | (% by wt.) |
| Disodium lauryl ether sulfosuccinate | 5.00 | |
| Decyl glucoside (P.D.: =1.5) | 2.00 | |
| PEG-55-propylene glycol oleate | 2.00 | |
| PEG-3-distearate (opacifier) | 1.90 | |
| Panthenol | 0.30 | |
| Lactic acid | 0.10 | |
| Citric acid | 0.20 | |
| Pyrrolidone carboxylic acid | 0.10 | |
| Tartaric acid | 0.10 | |
| Glyoxylic acid | 0.05 | |
| Pyruvic acid | 0.10 | |
| Malic acid | 0.03 | |
| Stinging nettle oil | 0.10 | |
| Glycerol | 1.00 | |
| Perfume | 0.30 | |
| Octopirox ® (anti-dandruff active) | 0.40 | |
| Preservatives | 0.35 | |
| Allantoin | 0.10 | |
| Sodium chloride | 1.80 | |
| Water | @ 100.00 | |

EXAMPLE 6

| Shampoo for greasy hair | | |
|---|---|---|
| Sodium lauryl ether sulfate | 9.00 | (% by wt.) |
| Decyl glucoside (P.D.: =1.5) | 2.00 | |
| PEG-3-distearate (opacifier) | 1.50 | |
| Panthenol | 0.30 | |
| Thyme oil | 0.10 | |
| Lactic acid | 0.15 | |
| Citric acid | 0.40 | |
| Pyrrolidone carboxylic acid | 0.10 | |
| Tartaric acid | 0.10 | |
| Glycolic acid | 0.05 | |
| Malic acid | 0.10 | |
| Pyruvic acid | 0.10 | |
| Polyethylene glycol-6-isolauryl thioether in cetyl alcohol | 4.00 | |
| Glycerol | 2.00 | |
| Allantoin | 0.30 | |
| Perfume | 0.60 | |
| Preservatives | 0.35 | |
| Sodium chloride | 2.00 | |
| Water | @ 100.00 | |

We claim:
1. A hair shampoo composition comprising at least 5% to 50% by weight of the total composition of at least one anionic surfactant, and a mixture of a) at least 0.1% by wt. lactic acid;

b) at least 0.05% by wt. citric acid; and c) at least 0.05% by wt. pyrrolidone carboxylic acid; wherein all percentages are calculated by weight of the total composition.

2. The hair shampoo composition according to claim 1, further comprising at least 0.5% by wt. glycerol.

3. The hair shampoo compostion according to claim 1, further comprising at least one organic acid selected from the group consisting of glycolic acid, malic acid, glyoxylic acid, tartaric acid and pyruvic acid.

4. The hair shampoo composition according to claim 1, comprising at least 5% to about 40% by wt., of the at least one anionic surfactant.

5. A hair shampoo composition comprising at least 5% to 50% by weight of the total composition of: at least one of anionic surfactant selected from the group consisting of alkyl sulfates, ether sulfates, ethoxylated sulfates, monoglyceride sulfates, fatty acid amide sulfates, fatty acid alkanol amide sulfates and the alkali salts of said alkyl sulfates, said ether sulfates, said ethoxylated sulfates, said monoglyceride sulfated, said fatty acid amine sulfates, and said fatty acid alkanol amide sulfates, mono- and dialkyl phosphates, α-olefin sulfonates and salts of said mono- and dialkyl phosphates and said α-olefin sulfates sulfosuccinic acid semi-esters and alkali salts of said sulfoccinic acid semi-esters, monoalkyl ethoxysulfosuccinates, alkyl polyether carboxylic acids and alkali salts of said monoalkyl ethoxysulfosuccinates and said alkyl polyether carboxylic acids; nonionic surfactant selected from the group consisting of alkyl polyglucosides, fatty acid mono- and dialkanolarides, sorbitan esters, and condensates of ethylene oxide and propylene oxides; and amphoteric surfactant selected from the group consisting of fatty acid amido alkyl betaines, sulfobetaines and amido alkyl amino acids, and a mixture of a) at least 0.1% by wt. lactic acid;

b) at least 0.05% by wt. citric acid; and c) at least 0.05% by wt. pyrrolidone carboxylic acid; wherein all percentages are calculated by weight of the total composition.

6. The hair shampoo according to claim 5, further comprising at least 0.5% by weight glycerol.

7. The hair shampoo according to claim 5, further comprising at least one organic acid selected from the group consisting of glycolic acid, malic acid, glyoxylic acid, tartaric acid and pyruvic acid.

8. The hair shampoo according to claim 5, comprising 5% to about 40% by weight of the total composition of the at least one anionic surfactant.

9. The hair shampoo according to claim 8, wherein the at least one anionic surfactant is sodium lauryl ether sulfate.

10. The hair shampo according to claim 4, wherein the at least one anionic surfactant is sodium lauryl ether sulfate.

11. A hair shampoo composition comprising at least 5% to 50% by weight of the total composition of at least one anionic surfactant selected from the group consisting of alkyl sulfates, alkyl ether sulfates, ethoxylated sulfates, monoglyceride sulfates, fatty acid amide sulfates, fatty acid alkanol amide sulfates and the alkali salts of said alkyl sulfates, said alkyl ether sulfates, said ethoxylated sulfates, said monoglyceride sulfates, said fatty acid amide sulfates and said fatty acid alkanol amide sulfates, mono- and dialkyl phosphates, α-olefin sulfonates and salts of said mono- and dialkyl phosphates and said α-olefin sulfonates, sulfosuccinic acid semi-esters, monoalkyl ethoxysulfosuccinates and alkyl polyether carboxylic acids and alkali salts of said sulfocuccinic acid semi-esters, said monoalkyl ethoxysulfosuccinates and said alkyl polyether carboxylic acids; and a mixture of a) at least 0.1% by wt. lactic acid;

b) at least 0.05% by wt. citric acid; and c) at least 0.05% by wt. pyrrolidone carboxylic acid; wherein all percentages are calculated by weight of the total composition.

12. The hair shampoo according to claim 11, further comprising at least 0.5% by weight glycerol.

13. The hair shampoo according to claim 11, further comprising at least one organic acid selected from the group consisting of glycolic acid, malic acid, glyoxylic acid, tartaric acid and pyruvic acid.

14. The hair shampoo according to claim 11, comprising 5% to about 40% by weight of the total composition of the at least one anionic surfactant.

15. The hair shampoo according to claim 11, wherein the at least one anionic surfactant is sodium lauryl ether sulfate.

\* \* \* \* \*